United States Patent [19]

Naylor

[11] 4,124,822
[45] Nov. 7, 1978

[54] ISOLATION AMPLIFIER
[75] Inventor: Thomas K. Naylor, Belmont, Mass.
[73] Assignee: American Optical Corporation, Southbridge, Mass.
[21] Appl. No.: 833,932
[22] Filed: Sep. 16, 1977
[51] Int. Cl.² .............................................. H03F 3/38
[52] U.S. Cl. ..................................... 330/10; 330/166; 330/170; 330/171
[58] Field of Search ..................... 330/9, 10, 165, 166, 330/167, 170, 171

[56] References Cited
U.S. PATENT DOCUMENTS
3,946,324  3/1976  Smith ...................................... 330/10

Primary Examiner—James B. Mullins
Attorney, Agent, or Firm—Jeremiah J. Duggan; Stephen A. Schneeberger; Howard R. Berkenstock, Jr.

[57] ABSTRACT

A DC isolation amplifier having improved conductive isolation between its input and output. The amplifier includes an input section having a modulator and an output section having a demodulator and an oscillator section. The modulator and demodulator are nonconductively coupled through inductive loops of two closed-loop cores of magnetic material each having windings inductively coupled to the material of their associated core and to the other of the modulator or the demodulator. Additionally, a unitary closed loop winding couples the two cores such that the net EMF induced in the turns of the winding accordingly such that the respective component of the external magnetic field of the turns is substantially normal to the respective plane of each turn of this plurality. Additionally, this unitary loop is twisted between the cores to comprise a twisted pair additionally to minimize the effects from external magnetic fields. In the preferred embodiment, this loop is limited to two turns per core. However, this number may be increased slightly for certain specific situations. In preferred embodiments, the cores are housed in magnetic shields, the shields having an opening in one end and the center line of the core is disposed in the plane of the opening of the shield.

10 Claims, 10 Drawing Figures

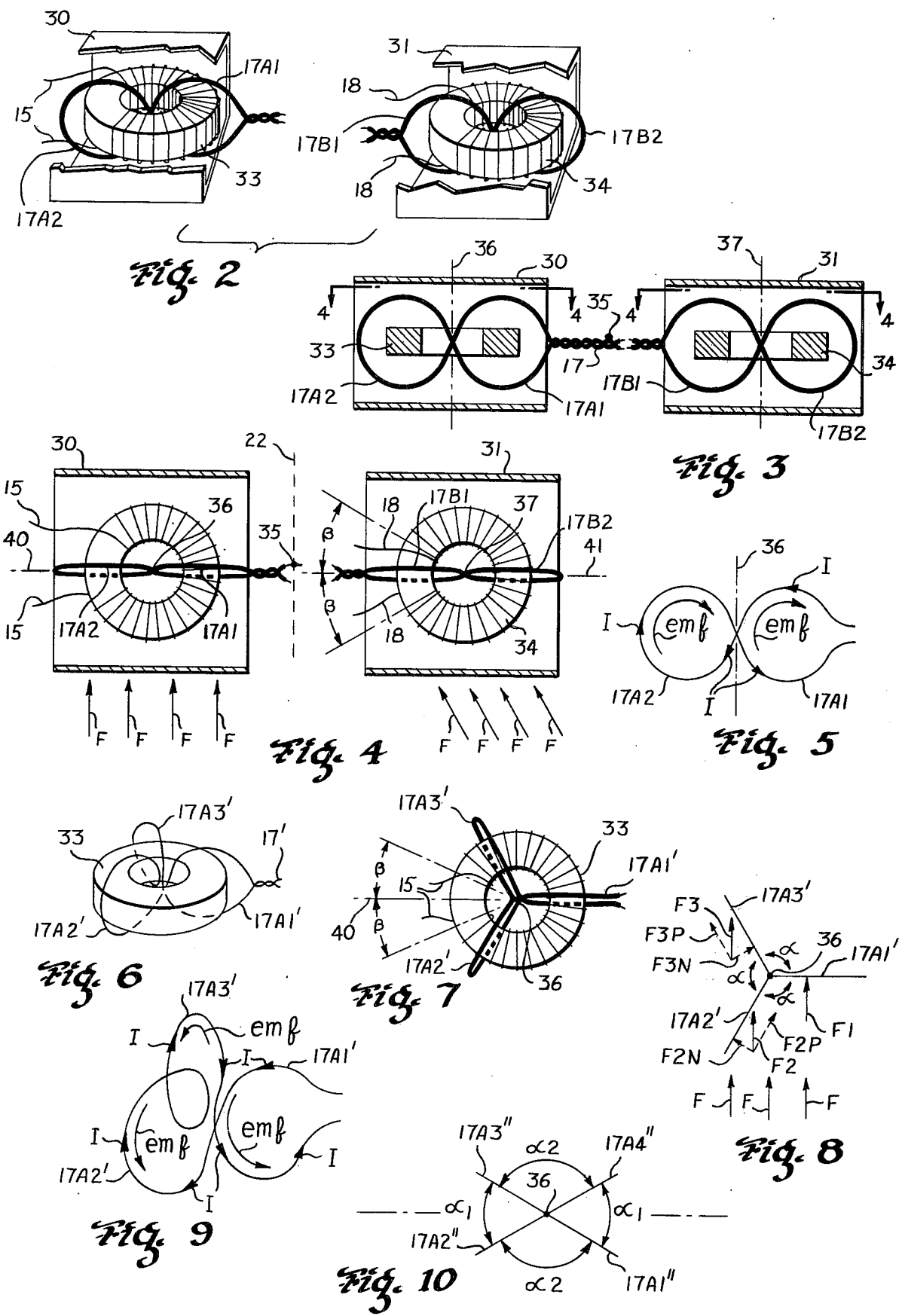

ISOLATION AMPLIFIER

BACKGROUND OF THE INVENTION

The invention relates to electronic amplifiers and more particularly to isolation amplifiers having substantially no DC conductive paths between the input terminals and any of the surrounding ground, output, or power supply circuits. More particularly still, the invention relates to improvements in such amplifiers which inductively couple a signal from an input section to an output section. This invention particularly relates to improvements in such isolation amplifiers as may be commonly utilized in the medical field.

Amplifiers have in the past been provided with circuit arrangements for effecting conductive isolation between different components or elements connected thereto. Although such amplifiers have served useful functions in some fields, typically they have not been capable of meeting the severe requirements of a number of unique and important applications. One such important application is in the medical field where for a variety of purposes electronic equipment must be connected to human patients to measure electrical impulses and the like, e.g. for taking electrocardiograms. It has become increasingly apparent that the conventional electronic equipment can, when connected to a human, cause serious injury or even death in the event of minor equipment malfunctions, operator error, or some other inadvertent event. Further, there are many other applications for high performance isolation amplifiers as for instance in the field of industrial process control where it becomes necessary to isolate the signal source from the system output.

One such isolation amplifier which generally meets the aforementioned requirements for isolation in the medical and/or process control field is described in U.S. Pat. No. 3,946,324. That isolation amplifier comprises an input portion for receiving the DC input signal and includes, in the input portion, an AC energized modulator to produce an AC signal substantially corresponding to the DC input signal. The amplifier further includes an output portion receiving the AC signal from the input portion, which output portion also includes a phase sensitive demodulator to produce a generally corresponding, relatively amplified DC output signal. A transformer serves to non-conductively couple the AC signal from the input portion to the output portion. The AC signal from the modulator and the phase sensitive detection thereof by the demodulator are controlled by an AC energizing signal from an AC power portion of the amplifier. The AC power portion includes circuitry for converting a DC power source to the AC energizing signal and further includes a transformer for non-conductively coupling the AC energizing signal to the input portion of the amplifier in order to activate the modulator. Further still, the AC energizing signal is connected or coupled to the demodulator in an appropriate phase relationship with the AC signal extended to the modulator.

The isolation amplifiers, while generally providing the degree of isolation required in the medical and other fields may, under certain circumstances, permit a degree of degradation of the signal transferred from the input to the output which may be unsuitable to the user's needs. For example, in the field of electrocardiography even very slight distortions in the output signal may be misinterpreted as normal or abnormal as the case may be. Because of the importance in interpreting such ECG signals, it is particularly important that the output signal be a faithful reproduction of the input signal from the patient's heart.

In providing the degree of high voltage isolation required in the medical and other fields, isolation amplifiers of the type described above have used a transformer arrangement to inductively, non-conductively couple the AC signal from the input portion to the output portion. More particularly, the transformer coupling arrangement has comprised two separate cores of magnetic material which are inductively coupled to one another by a single-turn winding and are respectively coupled to the output of the modulator and to the input of the demodulator. This arrangement permits a substantial spacing between the pair of magnetic cores thus permitting substantial physical separation between the corresponding primary and secondary windings associated with the modulator and demodulator respectively, and thereby provides effective isolation between those windings.

However, the aforedescribed single-turn coupling arrangement does exhibit certain limitations, particularly in the presence of external magnetic fields and also in situations in which even greater spacing between the magnetic cores is desired, the latter need being determined by housing geometry and/or the existance of particularly high potentials. It is not uncommon for the power supplies associated with the isolation amplifier and the accompanying load circuitry (e.g. a monitor) to create significant magnetic fields in the regions of the respective magnetic cores and the intermediate, single-turn winding connecting respective pairs of cores. Such magnetic fields may interact with the primary and secondary windings on the core-pair as well as with the intermediate, connecting winding extending between the core-pair, to induce emf's in the respective windings which distort the signal being conveyed from the input to the output. Clearly such distortion, even when very slight, may affect the appearance of an electrocardiographic or electroencephalographic signal or the like to such an extent that it may be misinterpreted as normal or as abnormal when in fact the reverse is true. Because of the importance in correctly interpreting such physiological signals, it is particularly important that the output signal be a faithful reproduction of the input signal from the patient's heart, brain, or the like.

Although optical coupling elements might be used to provide the requisite isolated coupling between input and output without interference from external magnetic fields, such optical coupling elements are particularly subject to drift and nonlinearities and are thus not ideal from DC use in physiological monitoring systems and the like.

Accordingly, it is a principal object of the present invention to provide an isolation amplifier of the type described having inductive coupling between the input and output and possessing improved fidelity in the transfer of the input signal to the output, particularly in the presence of magnetic fields.

It is another object of the present invention to provide an isolation amplifier utilizing inductive coupling between corresponding pairs of magnetic cores in a manner affording increased design flexibility.

These and other objects will be in part obvious and in part pointed out in greater detail hereinafter.

SUMMARY OF THE INVENTION

In accordance with the present invention there is provided an improved DC isolation amplifier of the type providing a high degree of conductive isolation between its input and output, the amplifier including an input section, an output section and an oscillator section, the input section having a modulator to produce an AC signal corresponding to the DC input signal, the output section having a demodulator adapted to receive the AC signal from the modulator and to produce a corresponding DC output signal therefrom and the oscillator section producing an AC energizing signal for the modulator and demodulator. First and second circuit means respectively non-conductively couple the AC signal from the modulator to the demodulator and the AC energizing signal from the oscillator to the input section. Third circuit means couple the AC energizing signal from the oscillator to the demodulator in the output section. At least the first non-conductive coupling means comprises first and second substantially closed-loop cores of magnetic material, each core having a respective center-line extending through the central opening thereof, the cores being physically separated by a substantial distance and each carrying a winding inductively coupled to the magnetic material of the associated core and associated with a respective one or the other of the modulator and demodulator. Conductor means link the first and second cores and inductively couple the magnetic paths thereof in an improved manner which minimizes the net emf induced in the conductor means as a result of external magnetic fields.

More particularly, the improvement comprises the conductor means forming a unitary closed-loop linking each of the first and second cores with a plurality of turns, each of the turns having a portion passing through the central opening of a respective one or the other of the first and second cores and the plurality of turns associated with one or the other of the first and second cores being arranged relative to one another about the center-line of the respective coil to minimize the net emf induced in the plurality of turns by the respective component of an external magnetic field substantially normal to the respective plane of each turn of the plurality. Furthermore, the conductor means is additionally twisted between the first and second cores to comprise a twisted pair for also minimizing the effects thereon of external magnetic fields.

In a preferred embodiment of the invention, the plurality of conductor turns associated with each core is limited to two turns per core. However, in other embodiments the number of conductor turns per core may be three or possibly a few more. The conductor means linking the first and second cores typically comprises conventional insulated wire, the insulation being able to withstand high voltages, for instance 10 kilovolts or more. In the embodiment comprising two conductor turns per core, both turns are in the same plane and disposed at 180° to one another about the center-line of the respective core. In an embodiment comprising three conductor turns per core each turn is arranged in a separate plane disposed at 120° to the planes of the other turns about the center-line of the respective core.

In accordance with a still further aspect of the invention, each of the two cores comprising the coupling transformer between the modulator and demodulator is housed in a respective magnetic shield, each shield having an opening in at least one end thereof. A plane including the center-line of the respective core extends through substantially the center of the shield opening to define a reference plane and the winding inductively coupled to the respective core associated with a respective one or the other of the modulator and demodulator is symmetrically disposed on opposite sides of the reference plane to minimize the emf inducted in the windings by an external magnetic field passing through the shield opening. Further still, the plurality of conductor turns associated with a respective one or the other of the first and second cores are respectively sized and angularly oriented about the core center-line such that the areas thereof projected parallel to the reference plane onto a plane substantially normal to the reference plane and parallel to the core center-line are equal on opposite sides of the reference plane. In the preferred embodiment comprising two conductor-turns per core, those two conductor turns-lie substantially in the reference plane extending substantially normal to the shield opening.

BRIEF DESCRIPTION OF THE DRAWINGS

FIG. 2 is a perspective view, with parts broken away, of the improved transformer coupling arrangement of the invention;

FIG. 3 is a vertical section taken through the respective center-lines of the pair of cores and magnetic shields comprising the transformer coupling arrangement of the invention;

FIG. 4 is a sectional plan view of the core-pair taken along lines 4—4 of FIG. 3;

FIG. 5 is a diagrammatic illustration of the emf's induced by an external magnetic field in the two turns of the core-coupling conductor associated with one of the cores;

FIG. 6 is a perspective view of one of the cores and its core-coupling turns in accordance with another embodiment of the invention;

FIG. 7 is a plan view of the core and conductor of FIG. 6;

FIG. 8 is a diagrammatic plan view of the core-coupling turns of the FIG. 6 embodiment, showing an external magnetic field applied thereto;

FIG. 9 is a diagrammatic perspective view of the three conductor-turns of the FIG. 6 embodiment illustrating the emf's induced by the external field; and FIG. 10 is a diagrammatic plan view of the core-coupling turns associated with a respective core in a further embodiment of the invention.

DESCRIPTION OF THE PREFERRED EMBODIMENTS

Figure 1:
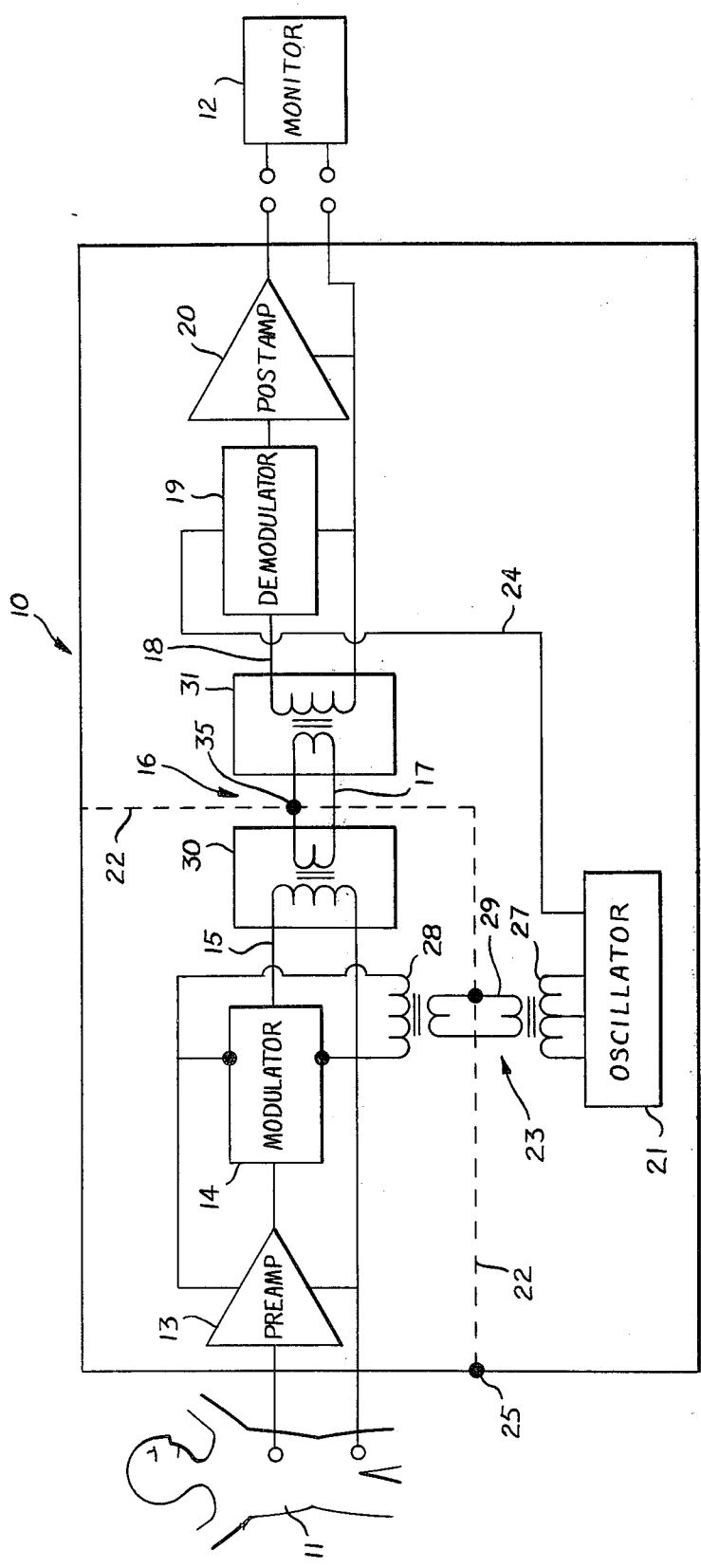
FIG. 1 is a symbolic block diagram of an isolation amplifier in accordance with the invention and utilized in a patient monitoring system.

Referring now to FIG. 1, there is illustrated the improved isolation amplifier 10 of the invention for use in extending physiological information signals from a patient 11 to a monitor 12 or the like. Isolation amplifier 10 is, in most respects, the same as that disclosed in the aforementioned U.S. Pat. No. 3,946,324 and also that disclosed in U.S. patent application Ser. No. 757,166 filed Jan. 6, 1977, now Pat. No. 4,075,572, by George A. Cavigelli for Isolation Amplifier Having Improved Fidelity, both of which are incorporated herein by reference. Generally speaking, isolation amplifier 10 receives a DC or a slowly varying DC signal from patient 11 which is in turn connected to the input of a preamplifier 13. Preamplifier 13 amplifies the input signal and extends it to the input of an AC modulator 14. Modulator 14 is arranged to produce an AC pulse signal having an amplitude corresponding to the magnitude of the DC signal on the inputt to amplifier 10. This modulator may be a half-wave FET circuit arranged as a switch in series with a transformer primary 15. The primary 15 forms part of an isolation transformer generally indicated at 16. The structure of isolation transformer 16 comprises the subject of the present invention and will be described hereinafter in greater detail. Suffice it now to say that an intermediate winding 17 serves to inductively non-conductively couple the primary 15 to the secondary winding 18.

The transformer secondary winding 18 comprises an input to a demodulator 19 which, like modulator 14, may comprise a half-wave FET circuit arranged as a switch in series with the secondary 18. The output from demodulator 19 may be applied to a postamplifier 20, the output of which is then available for application to a load circuit, such as monitor 12.

An oscillator 21 may be battery-powered and generates a substantially squarewave form, preferably in the manner described in the aforementioned U.S. application Ser. No. 757,166. The squarewave then serves as an AC energizing signal which is inductively coupled to the input section 22 of isolation amplifier 10 by means of a second isolation transformer 23. This squarewave AC energizing signal, when coupled to input section 22, provides a supply voltage for the preamplifier 13 and additionally serves to control switching operation of modulator 14 in a synchronized manner. Further still, the AC squarewave signal is coupled to the demodulator 19, as by conductor 24, to control the switching operating of the demodulator in synchronization with modulator 14.

Both isolation transformers 16 and 23 serve the function of conductively isolating the amplifier input section 22 from the remaining circuitry such as oscillator 21, demodulator 19 and monitor 12. In this way no DC connection will exist between the input to isolation amplifier 10 any any of the surrounding ground, output or power supply circuits. In the illustrated embodiment, the isolated input section of isolation amplifier 10 lies within the dotted lines represented by the numeral 22. Dotted line 22 is additionally intended to indicate an electrostatic shield structure which is electrically connected to a circuit guard terminal 25 which may be connected to the patient 11.

Referring briefly to the operation of isolation amplifier 10 the switch of modulator 14 is opened and closed alternately by the squarewave AC signal coupled from the oscillator 21 via isolation transformer 23 so as to create a modulated carrier in the primary winding 15 of isolation transformer 16. The amplitude of this modulated carrier is determined by the amplitude of the DC input signal from patient 11. The modulated carrier in primary 15 develops in secondary 18 (via intermediate winding 17) a modulated carrier, the pulses of which have an amplitude also corresponding to the magnitude of the DC input signal from patient 11. This modulated AC signal on secondary 18 serves to produce a DC output signal from demodulator 19 corresponding to the original DC input signal from patient 11. This demodulation is accomplished by the synchronized switching effected by the squarewave signal from oscillator 21.

Isolation transformer 23, like isolation transformer 16, includes a primary winding 27, a secondary winding 28 and an intermediate winding 29. More particularly, each of the isolation transformers 16, 23 comprises two separate cores, one for the primary and one for the secondary. Each core is made of magnetic material (ferrite) arranged as a toroid, and is wrapped with the coils of the corresponding winding. All of the cores are physically disposed with their respective center-lines (the toroidal axes) perpendicular to a horizontally disposed circuit mounting board (not shown). Typically, primary winding 15 and secondary winding 18 of transformer 16 are comprised of the same number of turns, i.e., 50 turns. Because the primary 27 of transformer 23 is center-tapped, secondary 29 will normally have half as many windings as the primary. Accordingly, primary 27 may have 76 turns and secondary 28 may have 38 turns. However, in accordance with the present invention, the primary windings of transformers 16 and 23 are coupled to the respective secondaries thereof by respective intermediate windings 17 and 29 which differ from the intermediate winding arrangements of the aforementioned prior art. Inasmuch as the construction of transformer 23 is essentially the same as that of transformer 16 in the present invention, only the structure of transformer 16 will be described hereinafter in greater detail. A remaining distinction does reside in the fact that transformer 16 may be provided with magnetic shields 30 and 31 according to one aspect of the invention, whereas transformer 23 may not require similar magnetic shields.

Referring to FIGS. 2-4, the primary winding 15 associated with the output of modulator 14 is wound on a first ferrite core 33 and the secondary winding 18 associated with demodulator 19 is wound on a second ferrite core 34. The intermediate winding 17 may be considered as being comprised of a pair of series-connected back-to-back plural-turn windings. In the FIGS. 2-4 embodiment, intermediate winding 17 includes two turns 17A1 and 17A2 about core 33 and two turns 17B1 and 17B2 about core 34. The intermediate winding 17 is electrically connected at junction 35 on its length to the electrostatic shield or guard 22.

The present intermediate winding 17 provides inductive coupling between primary 15 and secondary 18 in order to maintain high voltage, i.e. 7kv, DC isolation between the two. However, unlike the aforementioned prior art which provides only a single turn about each of the respective ferrite cores, the present intermediate windings provides a plurality of turns arranged to minimize the induction therein of unwanted emf's as a result of the presence of external magnetic fields arising from various power supplies in the system. It will be appreciated that the intermediate winding carries a current when inductively coupling the primary signal to the transformer secondary and that an external magnetic field oriented normal to the plane containing a single turn of the winding will induce an emf therein. The sense and magnitude of that emf will be determined by the orientation and magnitude of the magnetic field. It will be appreciated that the term "magnitude of the magnetic field" as used herein refers to the magnitude and direction of the rate of change of the magnetic field. Because such induced emf's are capable of distorting the meaningful information in the patient physiological signal, as by distorting the current in the intermediate winding, it is desirable that they be eliminated or at least minimized.

Accordingly, the two turns 17A1, 17A2 about core 33 and the two turns 17B1, 17B2 about core 34 are respectively wound and oriented to minimize the net emf induced in intermediate winding 17. Cores 33, 34 may each have an outside diameter of about ½ inch and an inside diameter of about ¼ inch. Intermediate winding 17 is comprised of conventional No. 22 insulated conductor wire, the insulation being selected to have a 15 kilovolt breakdown rating. The pair of turns 17A1, 17A2 (as also, 17B1, 17B2) are wound and oriented such that both turns lie in substantially the same plane, that plane being a vertical plane passing through the center-line (axis) 36 of core 33 (center-line 37 in core 34). The two turns 17A1, 17A2 are formed using a "twisted pair" technique such that the two turns form a figure "8" pattern in the vertical plane, as illustrated in FIG. 3. In other words, the conductor of intermediate winding 17 passes over one side of core 33, down along the center-line 36, beneath the core to the opposite side thereof, up along the opposite side, over the top of the core to the center-line and down and finally underneath the core at the side from which the initial entry was made. The resulting configuration is that of a figure "8" lying on its side, with one lobe of the "8" comprising one turn and the other lobe comprising the other turn.

If one considers an external magnetic field in which the magnetic flux is oriented substantially parallel to the plane of the two core-coupling turns, there is relatively little area for interaction between conductor and magnetic field. However, in the extreme example illustrated in the left half of FIG. 4, an external magnetic field is comprised of magnetic flux vectors F oriented normal to the plane containing the two turns 17A1, 17A2. In that instance the emf's induced in intermediate winding 17 might easily be a significant but for the fact that the two turns lying on opposite sides of core center-line 36 are so wound that the emf's induced in each turn are in opposing directions and thus tend to cancel one another. This is most clearly illustrated in the diagram of FIG. 5 which shows a current path indicated by arrows I in turns 17A1, 17A2 and the direction or sense of the induced emf's caused by the magnetic field having flux vectors normal to the plane of the turns 17A1, 17A2. It will be noticed that the direction of the magnetic field is constant for both turns, but because of the figure "8" configuration of the turns the induced emf's are in respectively opposite directions. Because these induced emf's are in bucking relationship, they tend to cancel one another and have minimal net effect on the physiological signal from patient 11. Assuming turns 17A1, 17A2 to be of identical size and shape, the bucking emf's should similarly be of equal magnitude.

Referring to the right half of FIG. 4, the magnetic flux vectors F are not exactly normal on the plane turns 17B1, 17B2 and thus the emf's induced in each turn might not be as large as those induced in turns 17A1, 17A2. However, because turns 17B1, 17B2 are in a common plane and wound in "twisted-pair" or opposing relationship, the emf's will tend to cancel one another.

A still further advantage is obtained by tightly twisting the intermediate winding 17 in the region between cores 33 and 34. Applying the "twisted-pair" configuration in this region similarly helps to reduce the generation of emf's by stray external magnetic fields.

The use of two turns 17A1, 17A2 rather than the prior art single turn for the intermediate winding additionally reduces the effective impedance of the intermediate winding by a factor of four, which permits longer runs of the conductor to be made between cores 33 and 34. This has the advantage of permitting increased spacing between cores 33 and 34 (e.g. 3–6 inches or more) for flexibility of the overall mechanical design and also to increase the surface creepage path of leakage currents over winding 17.

According to another aspect of the invention, cores 33, 34 are provided with respective magnetic shields 30, 31. These magnetic shields are of material having a high magnetic permeability, such as grain-oriented electrical steel or mu metal. Magnetic shields 30, 31 are here illustrated as four-sided structures which are open at opposite ends thereof. Shields 30, 31 have four mutually perpendicular sides which surround the top, the bottom and two opposite sides of the respective cores. Shields 30, 31 may each comprise singular structures or may each comprise a pair of opposed "C" shaped structures in vertical, closely abutting or overlapping relationship. Shields 30, 31 serve to a large extent to short-circuit the magnetic flux F caused by an external magnetic field when that flux is directed transverse to the shield (as opposed to being aligned with the opening at one or the other end thereof). Accordingly, the two turns 17A1, 17A2 are oriented on core 33 such that the vertical plane which contains them extends through the center-line 36 of the core and substantially through the center of the openings at opposite ends of magnetic shield 30. This plane is represented in FIG. 4 by the dotted line 40 passing through the end openings of shield 30 and center 36 of core 33, and by the dotted line 41 passing through the center 37 of core 34 the respective end openings of the magnetic shield 31.

It will be appreciated that the orientation of the external magnetic field may be such that the respective magnetic flux vectors F are not effectively short-circuited by the magnetic shields 30 or 31 but instead are substantially normal to the instance, the external magnetic flux may interact with the primary winding 15 and/or the secondary winding 18 to induce unwanted emf's in them also. Therefore, to minimize the effects of a magnetic field oriented substantially parallel to the plane 40 (or 41) and thus normal to the openings in the magnetic shields 30 (31), the primary and secondary windings 15 and 18 respectively are wound on their respective cores such that they are symmetrical to the respective reference planes 40, 41. Stated another way, if primary winding 15 is comprised of 50 turns for instance, 25 of those turns will be completed on one side of plane 40 and the remaining 25 turns will be on the other side of that reference plane as illustrated in FIG. 4.

More particularly, the angle over which the primary and secondary windings 15 and 18 extend about their respective cores on opposite sides of the respective reference planes 40, 41 are equal. The complement of this angle is represented by the angle $\beta$ in FIG. 4. The angle $\beta$ represents the angle from the reference plane 41 to either the start or the end of the transformer secondary winding 18 about the circumference of core 34. Thus it will be seen that the effective area of those turns of the winding 18 on one side of reference plane 41 projected parallel thereto to the plane of the opening in the magnetic shield 31 is substantially equal to that area projected by the turns of the winding appearing on the other side of the reference plane. Thus the emf's induced in the secondary (and primary) winding turns to the right of plane 41 (and plane 40) are substantially equal in magnitude and opposite in sense of the emf's induced in the left-side winding turns, thereby tending to cancel one another.

Referring now to FIGS. 6-9, there is illustrated a further embodiment of the invention in which the intermediate winding, here designated 17', between cores 33 and 34 includes three turns about each core rather than the two of the previous embodiment. In the interest of brevity only the turns 17A1', 17A2' and 17A3' associated with core 33 are illustrated. The configuaration of three turns per core in the intermediate winding 17' may be prompted by a desire to further decrease the effective impedance of the coupling wire to permit longer runs between cores 33 and 34. However, it will be appreciated that an increase in the number of turns may required either an increase in the size of core 33 and/or a commensurate reduction in the size of the conductor and insulator comprising winding 17' as well as a resulting increase in the stray capacitance. An increase in the stray capacitance tends to reduce the isolation and while probably not a problem for a three-turn configuration, it may become so if the number of turns is increased substantially. The three-turn configuration of FIGS. 6-9 is similarly formed to minimize the net enf induced in those turns by the presence of an external magnetic field, represented by flux vectors F in FIG. 8. The magnetic shield 30 has been removed in FIGS. 6-8 for the sake of clarity, but its presence is implied. The turns 71A1', 17A2' and 17A3' are formed by the same general over-and-under or "twisting" sequence used in forming the two turns of the FIG. 3 embodiment. However, the three vertical planes containing the three respective turns 17A1'-17A3' are angularly spaced from one another about the core-center 36 at equal angles $\alpha$ of 120°. Assuming each of the three turns to be of substantially the same size, it will be seen from an analysis of FIGS. 8 and 9 that an external magnetic field applied to the turns, even normal to the plane of one of the turns, will result in but minimal induced emf. For instance, if the magnetic field is normal to the plane of turn 17A1', as illustrated by vector F1, it will result in the induction of an emf in turn 17A1' of some maximum magnitude determined by the magnitude of the magnetic field and in the sense indicated by the respective arrow in FIG. 9. However, it will also be seen that the magnetic field vector F2 associated with turn 17A2' is resolvable into a component F2N normal to the plane of that turn and a component F2P in quadrature therewith and parallel to the plane of the turn. Because of angle $\alpha$ between adjacent turns 17A1' and 17A2' is 120°, the magnitude of the field component normal to loop 17A2' is one-half that of the principal vector F2 itself. Thus, the emf induced in loop 17A2' is of the sense indicated by the emf arrow in FIG. 9, but of one-half the magnitude of that appearing in loop 17A1'.

Similary, a magnetic field vector F3 associated with loop 17A3' is resolvable into a component F3N normal to that loop and a component F3P in quadrature therewith and parallel to the loop. Once again, because of the angles between loops 17A1', 17A2' and 17A3', the magnitude of the field vector F3N is only one-half that of F3 (and thus also F1). Therefore, the emf induced in loop 17A3' is of the sense illustrated in FIG. 9, but also only of one-half the magnitude of the emf induced in turn 17A1'. Therefore, the emf in turn 17A1' is opposed and cancelled by the cumulative emf's in turns 17A2' and 17A3', each being one-half the magnitude of the emf in turn 17A1'.

Referring to FIG. 7, it will be evident that it is impossible to align all three turns 17A1', 17A2' and 17A3' along the reference plane 40 to minimize their exposure to an external magnetic field which might be oriented normal to the opening in the magnetic shield (not shown). However, it will be appreciated in view of the discussion of the foregoing paragraph that minimization of the net emf induced by the external field is obtained so long as the projection of the area of the turns to one side of reference plane 40 parallel to the reference plane toward the shield opening is comparable with the similarly projected area of the turns on the other side of the reference plane.

Referring to FIG. 10, there is illustrated in diagrammatic form a still further embodiment of the invention in which the number of turns per core associated with the intermediate winding is four, those turns being designated 17A1'', 17A2'', 17A3'' and 17A4''. These turns are wound in the same manner as for the previously discussed plural-turns per core embodiments such that the emf's induced by an external magnetic field are substantially cancelled. However, it will be noted that, unlike the three turns per core embodiment, the angle between successive turns is not necessarily constant. In fact, it is only required that the projected area of the turns on one side of a magnetic force vector passing through the core center 36 be substantially equal to the area of the turns on the other side of that force vector and projected parallel thereto. This of course assumes a magnetic field vector extending in a substantially horizontal plane if the planes of the respective turns are vertical. Thus, assuming an even number of turns, the foregoing requisite is satisfied if each turn is opposed by a turn of comparable size on the opposite side of center-line 36, at 180° thereto. Thus, in FIG. 10, though angles $\alpha_1$ and $\alpha_2$ differ, their cumulative value is 180°.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. In a DC amplifier providing a high degree of conductive isolation between its input and output, said amplifier including an input section, an output section and an oscillator section, said input section including a modulator to produce an AC signal corresponding to the DC input signal, said output section including a demodulator adapted to receive said AC signal from said modulator and to produce a corresponding DC output signal therefrom and said oscillator section producing an AC energizing signal for said modulator and demodulator, first and second circuit means respectively non-conductively coupling said AC signal from said modulator to said demodulator and said AC energizing signal from said oscillator to said input section, third circuit means for coupling said AC energizing signal from said oscillator to said output section, at least said first non-conductive coupling means comprising first and second substantially closed-loop cores of magnetic material, each said core having a respective center-line extending through the central opening thereof, said cores being physically separated by a substantial distance and each carrying a winding inductively coupled to the magnetic material of the associated core and associated with a respective one or the other of said modulator and demodulator, and conductor means linking said first and second cores and inductively coupling the magnetic paths thereof, the improvement wherein said conductor means forms a unitary closed-loop linking each of said first and second cores with a plurality of turns, each said turn having a portion passing through the central opening of a respective one or the other of said first and second cores, said plurality of turns associated with one or the other of said first and second cores being arranged relative to one another about the center-line of the respective said core to minimize the net emf induced in said plurality of turns by the respective component of an external magnetic field substantially normal to the respective plane of each turn of said plurality.

2. The apparatus of claim 1 wherein said plurality of conductor turns associated with each said core is limited to two turns per core.

3. The apparatus of claim 2 wherein said conductor means linking said first and second cores comprises conventional insulated wire, the insulation being able to withstand voltages of at least 10 kilovolts.

4. The apparatus of claim 2 wherein said two conductor turns are substantially entirely in the same plane and disposed at 180° to one another about the center-line of the respective core.

5. The apparatus of claim 1 wherein said plurality of conductor turns associated with each said core is limited to three turns per core.

6. The apparatus of claim 5 wherein said three conductor turns are each substantially in three respective planes each disposed at 120° to the others about the center-line of the respective core.

7. The apparatus of claim 1 wherein said conductor means is additionally twisted between said first and second cores to comprise a twisted pair for minimizing the effects of external magnetic fields.

8. The apparatus in claim 1 wherein each said core is housed in a respective magnetic shield, each said shield having an opening at at least one end thereof, a plane including said center-line of said respective core extends through substantially the center of said shield opening to define a reference plane, and said winding inductively coupled to the respective core associated with a respective one or the other of said modulator and demodulator is symmetrically disposed on opposite sides of said reference plane to minimize the emf induced in said windings by an external magnetic field passing through said shield opening.

9. The apparatus in claim 8 wherein said plurality of conductor turns associated with a respective one or the other of said first and second cores are respectively sized and angularly oriented about said core center-line such that the areas thereof projected a parallel to said reference plane onto a plane substantially normal to said reference plane and parallel to said core center-line are equal on opposite sides of said reference plane.

10. The apparatus of claim 8 wherein said plurality of conductor turns associated with each said core is limited to two turns per core, said two conductor turns are substantially entirely in the same plane and disposed at 180° to one another about the center-line of the respective core and substantially in said reference plane passing through said shield opening.

* * * * *